United States Patent
Samuel et al.

(10) Patent No.: US 11,517,900 B2
(45) Date of Patent: Dec. 6, 2022

(54) MICROFLUIDIC SYSTEM FOR SPERM SEPARATION AND ENRICHMENT FROM VARIOUS TYPES OF SPERM SAMPLES

(71) Applicant: University of Utah Research Foundation, Salt Lake City, UT (US)

(72) Inventors: Raheel Samuel, Salt Lake City, UT (US); Bruce Gale, Salt Lake City, UT (US); Alex Jafek, Salt Lake City, UT (US); Timothy Jenkins, Salt Lake City, UT (US); Jim Hotaling, Salt Lake City, UT (US); Douglas Carrell, Salt Lake City, UT (US); Jiyoung Son, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1045 days.

(21) Appl. No.: 16/173,934

(22) Filed: Oct. 29, 2018

(65) Prior Publication Data
US 2019/0329256 A1 Oct. 31, 2019

Related U.S. Application Data

(60) Provisional application No. 62/578,261, filed on Oct. 27, 2017.

(51) Int. Cl.
*B01L 3/00* (2006.01)
*C12N 5/076* (2010.01)
(Continued)

(52) U.S. Cl.
CPC ... *B01L 3/502761* (2013.01); *B01L 3/502776* (2013.01); *C12N 5/061* (2013.01);
(Continued)

(58) Field of Classification Search
CPC ..... B01L 2200/0636; B01L 2200/0647; B01L 2200/0668; B01L 2300/044;
(Continued)

(56) References Cited

U.S. PATENT DOCUMENTS 8,186,913 B2   5/2012   Toner et al.
9,523,075 B2   12/2016  Takayama et al.
(Continued)

FOREIGN PATENT DOCUMENTS

CN   2010/03051 Y    1/2008
CN   101210220 A     7/2008
(Continued)

OTHER PUBLICATIONS

Eravuchira et al.; "Individual Sperm Selection by Microfluidics Integrated with Interferometric Phase Microscopy." Methods; Elsevier; vol. 136; Mar. 1, 2018; pp. 125-159.

*Primary Examiner* — Jennifer Wecker
(74) *Attorney, Agent, or Firm* — Thorpe North and Western LLP

(57) ABSTRACT

A method for separating and enriching sperm from a tissue sample comprises: obtaining a microfluidic separating system having an inlet end and an outlet end, and a membrane filter (e.g., hollow fiber membrane filter) fluidly connected to the outlet end; separating the tissue sample via the microfluidic separating system into a debris fluid volume and a sperm fluid volume; and enriching the sperm fluid volume by removing excess media via the membrane filter. A two-stage tissue sample separation system comprising: a microchannel structure defining a separation fluid channel to form a separation stage; an inlet end of the microchannel structure; an outlet end of the microchannel structure; and a
(Continued)

membrane filter fluidly connected to the outlet end for removal of at least a portion of excess media in the tissue sample.

24 Claims, 7 Drawing Sheets

(51) Int. Cl.
  *G01N 1/40* (2006.01)
  *G01N 1/34* (2006.01)
(52) U.S. Cl.
  CPC ............. *G01N 1/34* (2013.01); *G01N 1/4077* (2013.01); *B01L 2200/0636* (2013.01); *B01L 2200/0647* (2013.01); *B01L 2300/044* (2013.01); *B01L 2300/047* (2013.01); *B01L 2300/049* (2013.01); *C12N 2503/00* (2013.01); *G01N 2001/4088* (2013.01)
(58) Field of Classification Search
  CPC ......... B01L 2300/047; B01L 2300/049; B01L 2300/0681; B01L 2300/0816; B01L 2300/0864; B01L 3/502761; B01L 3/502776; C12N 2503/00; C12N 2521/00; C12N 5/061; C12N 5/0612; G01N 1/34; G01N 1/4005; G01N 1/4077; G01N 2001/4088

See application file for complete search history.

(56) References Cited

U.S. PATENT DOCUMENTS

| | | | |
|---|---|---|---|
| 9,757,726 | B2 | 9/2017 | Sharpe et al. |
| 2006/0270021 | A1* | 11/2006 | Takayama ........... B01L 3/50273 |
| | | | 435/283.1 |
| 2010/0291535 | A1 | 11/2010 | Yao et al. |
| 2014/0315281 | A1 | 10/2014 | Pan |
| 2016/0290913 | A1 | 10/2016 | Demirci et al. |
| 2018/0119087 | A1 | 5/2018 | Lam et al. |
| 2018/0266937 | A1 | 9/2018 | Wagenaar et al. |
| 2018/0282676 | A1 | 10/2018 | Vollmer |

FOREIGN PATENT DOCUMENTS

| | | | | |
|---|---|---|---|---|
| CN | 202786220 U | | 3/2013 | |
| WO | WO-2015077333 A1 | * | 5/2015 | ........ B01L 3/502753 |
| WO | WO-2015084676 A1 | * | 6/2015 | .......... F04B 11/0025 |
| WO | WO-2016064896 A1 | * | 4/2016 | ........... A61B 17/435 |
| WO | WO-2016176563 A1 | * | 11/2016 | ............. C12M 47/04 |
| WO | WO-2017015574 A1 | * | 1/2017 | ............... C12Q 1/04 |
| WO | WO 2017/127775 A1 | | 7/2017 | |

* cited by examiner

MICROFLUIDIC SYSTEM FOR SPERM SEPARATION AND ENRICHMENT FROM VARIOUS TYPES OF SPERM SAMPLES

RELATED APPLICATION(S)

This application claims benefit to U.S. Provisional Patent App. No. 62/578,261 filed Oct. 27, 2017, which is incorporated herein by reference.

GOVERNMENT INTEREST

This invention was made with government support under Grant No. 1549659 awarded by the National Science Foundation. The government has certain rights in the invention.

BACKGROUND

Microsurgical testicular sperm extraction (MicroTESE) is a commonly utilized technique to treat patients with certain forms of non-obstructive azoospermia (NOA). The microTESE procedure is effective at identifying distinct loci at which spermatogenesis is likely to occur in testes that are otherwise void of sperm. Such targeted searching for sperm reduces the total volume of biopsy that is needed to screen for the presence of gametes. Despite the targeted screening of the testes performed in the microTESE, there remains a large amount of tissue (from testicular biopsies) to be searched under a scope that typically requires 10+ man hours of scope time. This cumbersome process is often not financially viable from the laboratory perspective. Human error is also common with traditional screening and separation techniques, because a technician must manually search through thousands of microscopic fields for rare sperm cells (as few as 20 per patient) within a heterogeneous cell population. Low sperm recovery rates are often the result of difficulties in locating and separating sperm cells from somatic cell types.

SUMMARY

The present disclosure sets forth a method of separating and enriching sperm from a tissue sample comprising: (a) obtaining a microfluidic separating system having an inlet end and an outlet end, wherein a membrane filter is fluidly connected to the outlet end; (b) separating the tissue sample via the microfluidic separating system into a debris fluid volume and a sperm fluid volume; and (c) enriching the sperm fluid volume by removing excess media via the membrane filter.

The present disclosure also sets forth a two-stage tissue sample separation system comprising: a microchannel structure defining a separation fluid channel to form a separation stage; an inlet end of the microchannel structure; an outlet end of the microchannel structure; and a membrane filter fluidly connected to the outlet end (the membrane filter defining an enrichment stage downstream of the separation stage). Accordingly, flow of the tissue sample through the separation stage facilitates at least partial segregation of materials in the tissue sample based on size, and subsequent flow of the tissue sample through the enrichment stage further facilitates removal of at least a portion of excess media in the tissue sample via the membrane filter.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
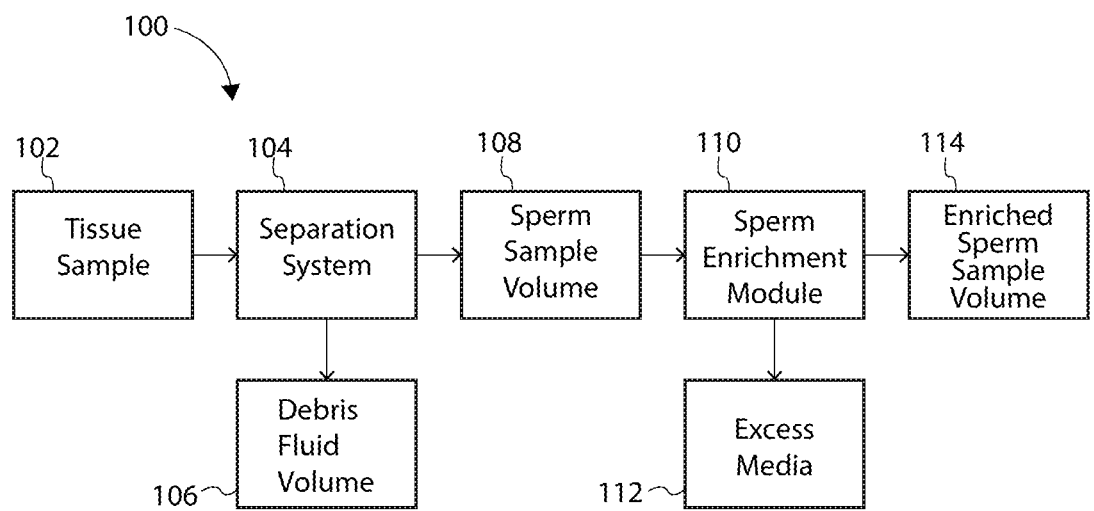
FIG. 1 is a flow chart illustrating a separation and enrichment system and method, in accordance with an example of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a particle" includes reference to one or more of such materials and reference to "subjecting" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 5%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Microfluidic System for Sperm Separation and Enrichment from Various Types of Sperm Samples A system can separate sperm from a heterogeneous mixture and enrich the separated sperm by removing excess media, which can be achieved without any chemical labeling (e.g. no labeling, no fluorescence source or detectors, etc). Notably, separation and enrichment can be achieved within twenty minutes through the approaches and systems exemplified herein. This is approximately a 97% reduction in time compared to traditional manual separation techniques. The systems and methods described herein can be used in a variety of environments including, but not limited to, sperm sample preparation for infertility clinics, and forensics. The systems described herein can be designed to be automatic for separation and enrichment of a sperm sample, which eliminates the need for humans to manually separate sperm samples individually under a microscope, because the present separation and enrichment systems and methods described herein provide a reliable, automated sperm collection and concentration system, thereby providing consistently increased sperm recovery rates irrespective of sperm motility.

FIG. 1 schematically illustrates a system and method for separating and enriching sperm from a tissue sample, which is collectively labeled as system 100, in accordance with an example of the present disclosure. The system 100 can comprise a tissue sample 102, such as a sperm tissue sample that was surgically removed from a human male, which may include a carrier fluid. In one example, the tissue sample 102 could be approximately 1 ml to 15 ml of sperm cells, red blood cells, tissue debris, and a carrier fluid. The tissue sample 102 can be injected and flowed into a microfluidic separating system 104 for separating materials of the tissue sample 102 into a debris fluid volume that can be deposited or collected in at least one collector 106. The at least one collector 106 can receive a number of different types of separated categories, such as media debris (RBCs), purged material, waste material, recyclable material, etc. The microfluidic separating system 104, defining a separation stage of the system 100, can further separate the tissue sample 102 into a sperm sample volume 108, which can include about 0.5 ml of sperm, red blood cells, media debris, etc. The sperm sample volume 108 can then be flowed through a sperm enrichment module 110 having a membrane filter (see below), which defines an enrichment stage of the system 100 for filtering and enriching the sperm sample volume 108. Thus, the sperm enrichment module 110 is operable to filter and discharge excess media to a collector 112, and operable to generate an enriched sperm sample volume 114. In this manner, excess media has been removed from the sperm sample volume 108 of the separated tissue sample 102, and without any loss (or noticeable loss) of sperm in the tissue sample 102. In some examples, the enriched sperm sample volume 114 can be increased by 40 to 60 times, meaning that excess media has been removed so that sperm cells are more easily counted and captured for use.

Figure 2:
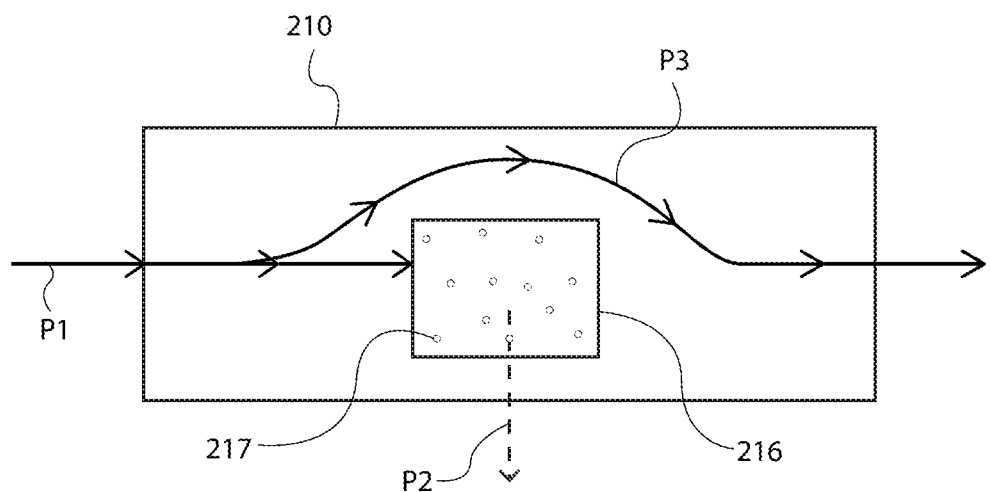
FIG. 2 schematically illustrates flow path of a sperm sample volume through a sperm enrichment module of a separation and enrichment system, in accordance with an example of the present disclosure.

FIG. 2 schematically (and generically) illustrates a sperm enrichment module 210 in accordance with an example of the present disclosure. The sperm enrichment module 210 can comprise a membrane filter 216, such as a hollow fiber membrane filter having pores 217, that operates to separate media debris from a sperm sample volume (e.g., 108) to enrich a sperm tissue sample (e.g., 102), thereby generating an enriched sperm sample volume (e.g., 114). Thus, the sperm enrichment module 210 can define a sperm sample volume flow path P1 through which a sperm sample volume is flowed to the membrane filter 216. The sperm enrichment module 210 can comprise or define an excess media flow path P2 defined by a flow path of excess media passing through the membrane filter 216, and then out from the membrane filter 216 for discharged to a collector (e.g., 112). The sperm enrichment module 210 can further comprise or define an enriched sperm fluid flow path P4 through which an enriched sperm sample volume is flowed or discharged after being flowed along or about the membrane filter 216 (to filter excess media from the sperm sample volume), which is further exemplified in the module of FIG. 3.

Figure 3:
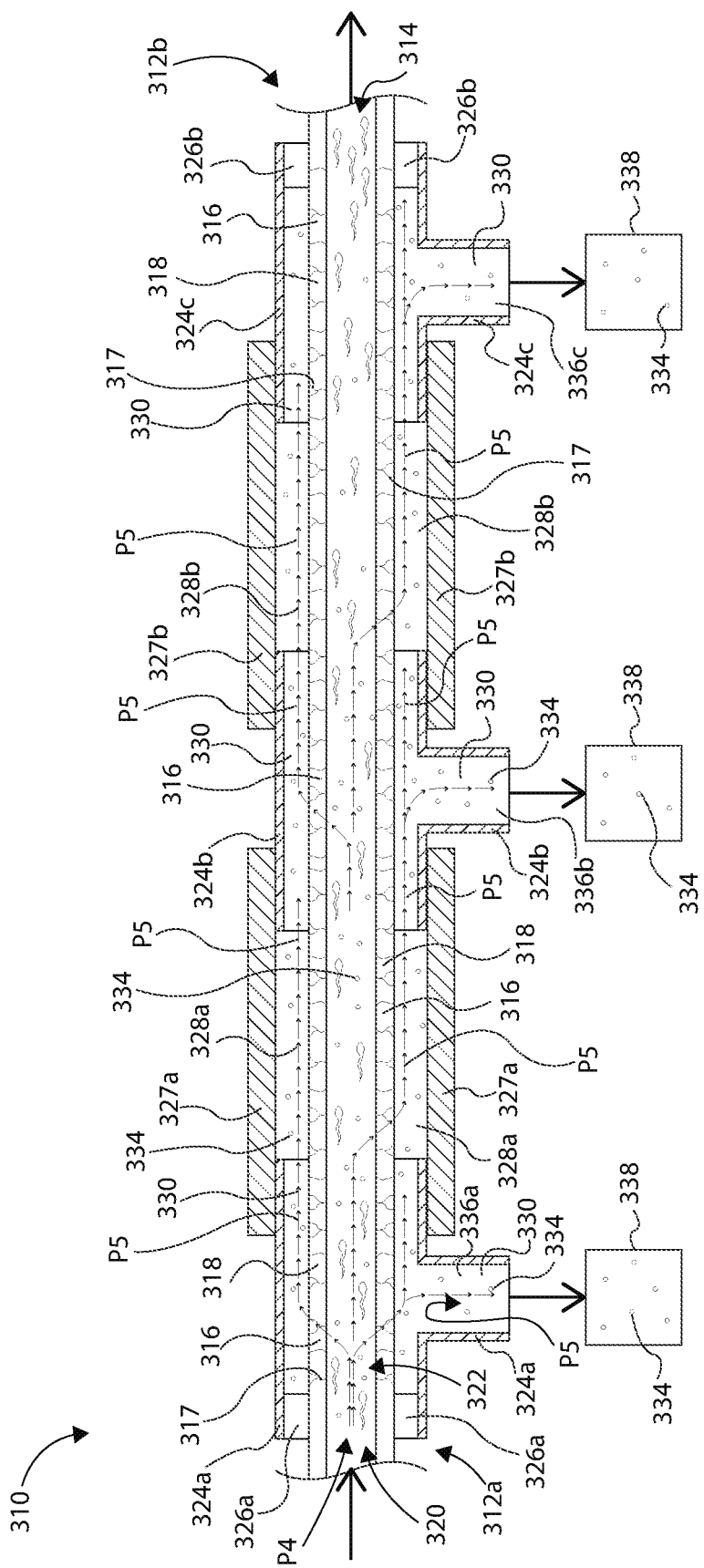
FIG. 3 is a cross sectional view of a sperm enrichment module, in accordance with an example of the present disclosure.

FIG. 3 is a cross sectional view of a sperm enrichment module 310 in accordance with an example of the present disclosure. The sperm enrichment module 310 can comprise an inlet end or zone 312a and an outlet end or zone 312b at opposing ends of the sperm enrichment module 310. A membrane filter 316 can extend a length of the sperm enrichment module 310 from the inlet zone 312a to the outlet zone 312b. The membrane filter 316 can be an elongate tube having a radial wall 318 at least partially comprised or formed of a hollow fiber membrane material. The membrane filter 316 can comprise a central passageway 320 through which a sperm sample fluid 322 is flowed into the inlet zone 312a and through the membrane filter 316. The sperm enrichment module 310 can further comprise a plurality of media discharge connectors 324a-c that can each be a T-port connector, for instance. The proximal media discharge connector 324a can be attached by an adhesive 326a to an outer surface of the membrane filter 316 proximate the inlet zone 312a, and the distal media discharge connector 324c can be attached by an adhesive 326b to an outer surface of the membrane filter 316 proximate the inlet zone 312b.

The sperm enrichment module 310 can further comprise first and second tube sections 327a and 327b (e.g., silicon tubing) that can interconnect or couple together the media discharge connectors 324a-c in series. In this manner, respective inner surfaces of the first tube section 327a can be attached (e.g., adhered) to outer surfaces first and second media discharge connectors 324a and 324b. Similarly, respective inner surfaces of the second tube section 327b can be attached (e.g., adhered) to outer surfaces second and third media discharge connectors 324b and 324c. The first and second tube sections 327a and 327b can each comprise an inner chamber area 328a and 328b that are in fluid communication with open areas 330 of the media discharge connectors 324a-c. The open areas 330 of the media discharge connectors 324a-c are defined by the area between inner surfaces of the T-port connectors, and an outer surface of the membrane filter 316. Note that a primary flow channel P4 extend centrally and longitudinally through the membrane filter 316 from the inlet and outlet zones 312a and 312b for passage of the sperm sample volume as it transitions to become an enriched sperm sample volume, as detailed below.

The radial wall 318 of the membrane filter 316 can comprise a hollow fiber membrane filter material, which is a porous material having microchannels or pores 317 (see also FIG. 2) sized to permit the passage of some materials based on size, such as excess media 334 (e.g., RBCs), and sized to restrict passage of other/larger materials, such as sperm cells, as graphically illustrated in FIG. 3. Thus, the membrane filter 316 is specifically designed for mammalian cell isolation. The pores 317 can have a pore size from 0.2 μm to 1 μm, in some cases from 2 to 5 μm, and in one example approximately 0.2 μm. In operation, a sperm sample volume 334 can be flowed into the sperm enrichment module 310, and which can contain a carrier fluid, sperm cells, red blood cells, and other media or debris. As the sperm sample volume 332 flows through the primary flow channel P4 of the membrane filter 316, an amount of fluid pressure (from back pressure) is exerted against the radial wall 318 of the membrane filter 316, so that smaller materials (e.g., RBCs) are forced or passed through the pores 317 of the membrane filter 316, while the (larger) sperm continues to flow along the primary flow channel P4 and through the central passageway 320 toward the outlet end or zone 324b. This filtering and enrichment process can define a tangential flow filtration system, because excess debris 334 of the sperm sample volume 322 can flow tangentially or radially through the membrane filter 316, and then to the open areas 330 of the media discharge connectors 324a-c, and then out through discharge outlets 336a-c of the media discharge connectors 324a-c. Such flow paths of excess media 334 are labeled as discharge flow pathways P5. The excess debris 334 can be collected as debris sample fluid 336 in one or more collectors 338.

The media discharge connectors 324a-c being arranged in series, and having two or more of such connectors 324a-c, provide a number of discharge outlets 336a-c that can collect and discharge the excess media along a length of the membrane filter 316. In this way, by the time that the sperm sample volume 322 has reached the outlet zone 312b, the sperm sample volume 322 has been enriched and transition to an enriched sperm sample volume 314, meaning that a noticeable amount of excess debris 334 has been filtered out and discharged away from the sperm sample volume 322 as is passes through the membrane filter 316. This is graphically illustrated by the lack of excess debris 334 shown near the outlet zone 312b, as compared to the amount of enriched sperm sample volume 314 that is flowed out proximate the outlet zone 312b. In one example, the sperm enrichment module 310 can remove ~450 μl of media while retaining ~50 μl of a purified or enriched sperm sample volume. Note that only one media discharge connector can be used in a similar device, or more than the three connectors shown in FIG. 3.

Figure 4:
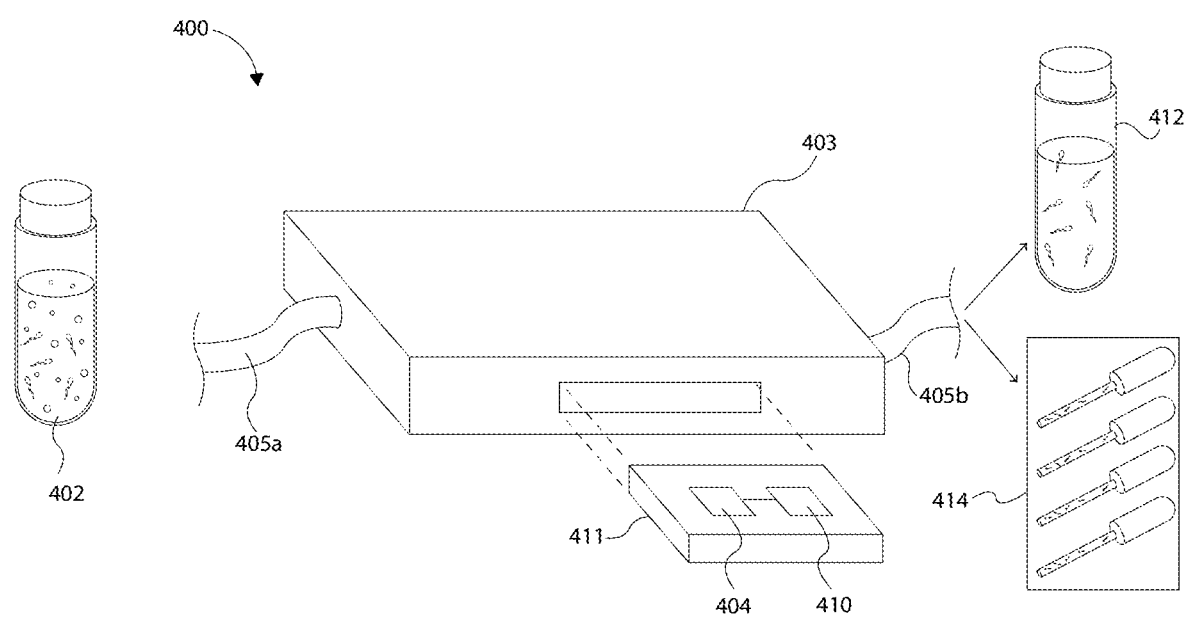
FIG. 4 illustrates a clinical implementation of a system and method for separating and enriching sperm from a tissue sample, in accordance with an example of the present disclosure.

FIG. 4 illustrates a system and method for separating and enriching sperm from a tissue sample from a clinical perspective, which is collectively labeled as system 400, in accordance with an example of the present disclosure. The system 400 can comprise a tissue sample 402 that can be injected or flowed into a base unit 403 via an input 405a. The base unit 403 can include a removable cassette or cartridge 411 that can include a microfluidic separating system 404 (e.g., 104, 304, 504) for separating materials of the tissue sample 402 into a debris fluid volume that can be deposited or collected in one or more collectors. The microfluidic separating system 404 can further separate the tissue sample 402 into a sperm sample volume that can then be flowed through a sperm enrichment module 410 (e.g., 110, 210, 310, 510), which can include a membrane filter for filtering the sperm sample volume. The sperm enrichment module 410 can be included as part of the removable cassette 411. Some or all of the microfluidic separating system 404 and/or the sperm enrichment module 410 can be supported by the removable cassette 411, which can take the form of a relatively small microfluidic chip. In this way, a (clean) removable cassette 411 can be quickly inserted into the base unit 403 for separating and enriching a sperm sample volume to generate an enriched sperm sample volume, and then the cassette 411 can be quickly removed and discarded after processing the sperm sample volume. Then, a new/clean cartridge can be inserted in to the base unit 403 for separating and enriching another sperm sample volume.

After processing, the enriched sperm sample volume can be collected in a storage container 412 and/or stored in cryotips 414 for cryogenic storage. Notably, small amounts of sperm, such as sperm in small aliquots (10-15 µl), can be stored in the cryotips while maintaining sperm viability compared to sperm cryopreserved in larger amounts (e.g., greater than 1 ml).

Figure 5:
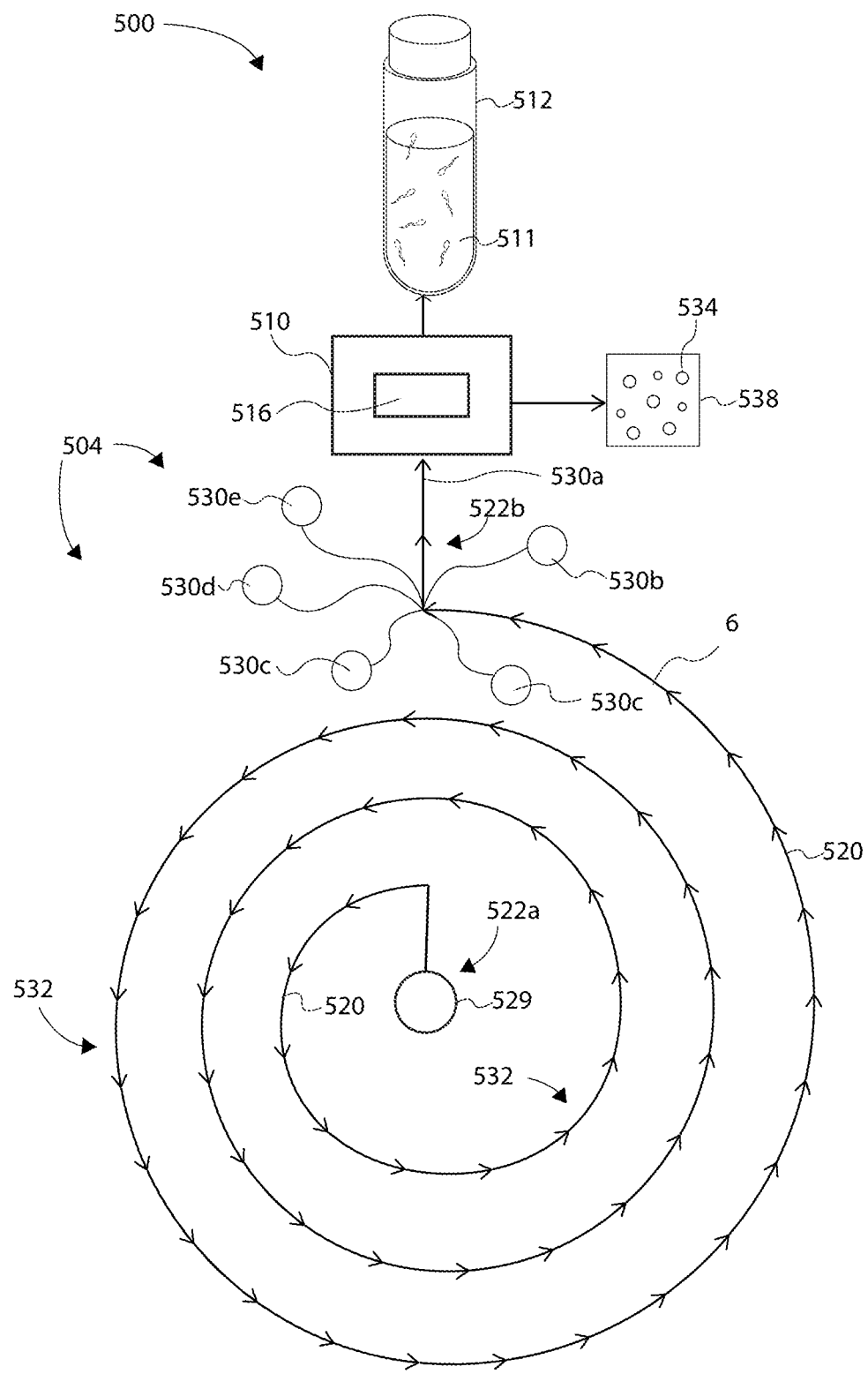
FIG. 5 illustrates a system and method for separating and enriching sperm from a tissue sample, in accordance with an example of the present disclosure.

FIG. 5 schematically illustrates another system and method for separating and enriching sperm from a tissue sample, which is collectively labeled as system 500, in accordance with an example of the present disclosure. The system 500 can comprise a microfluidic separating system 504 for separating materials of a tissue sample, which can include a microchannel structure 520 defining a separation fluid channel 507 (see FIG. 6). The microchannel structure 520 can have a spiral configuration, which can be formed or molded in polydimethylsiloxane (Slygard 184, Dow Corning, Mich.) and that is bonded to a double-sided glass slide by air plasma. The microfluidic separating system 504 can be similar or the same as described regarding PCT App. No. PCT/US15/56494, filed Oct. 20, 2015, which is incorporated by reference herein. As further described in such patent application, the microchannel structure 520 can comprise an inlet end or zone 522a proximate an inlet end 529 of the microchannel structure 520. The inlet end 529 can include a carrier fluid inlet to receive a carrier fluid and a tissue sample inlet to receive a tissue sample through one or more inlets of the inlet end 529. The microchannel structure 520 can include an outlet zone 522b having a plurality of outlets 530a-e.

The microchannel structure 520 can further comprise a transport region 532 between the inlet and outlet zones 522a and 522b. The transport region 532 can being open to the carrier fluid and the tissue sample, such that a cross-flow of fluid in the transport region 532 facilitates segregation of the materials in the tissue sample based on size, as further described in PCT App. No. PCT/US15/56494, incorporated herein. As cells and particles move through the microchannel structure 520, a counter rotating flow is established, which causes particles to move laterally in the channel. As the particles move towards the side walls of the channel 520, lift forces pushing the particles away from the wall cause the particles to move to an equilibrium position in the channel that balances the flow and lift forces. The location of this equilibrium position for particles in the channel depends on the size of the particles, their shape, the flow rate, and the geometry of the spiral channels. Thus, the spiral microchannel structure 520 can be used to separate immotile sperm from red blood cells.

Figure 6:
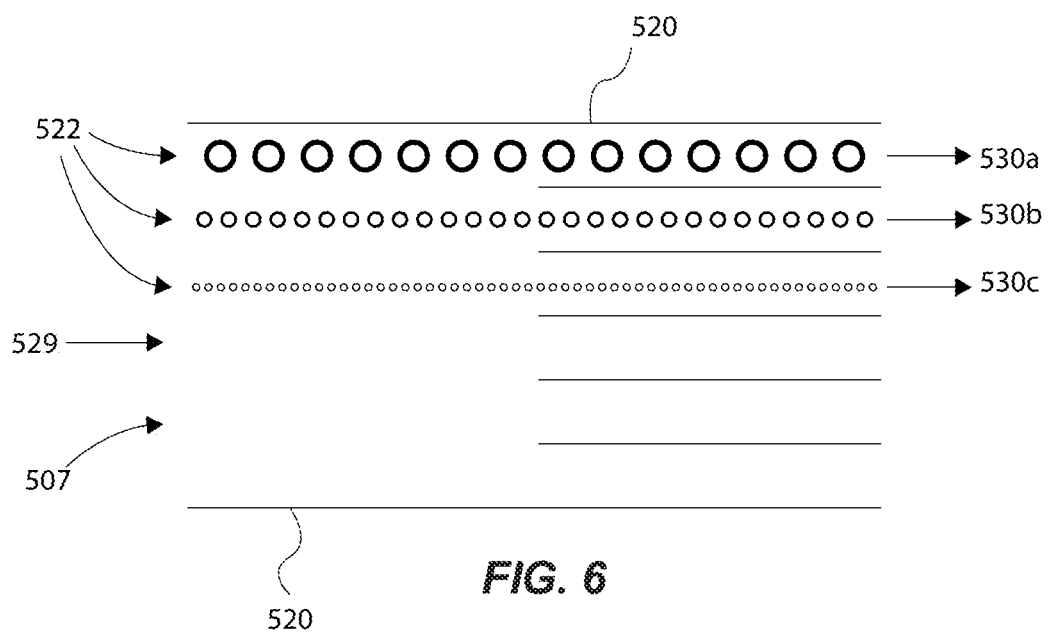
FIG. 6 is a side cross sectional view of a portion of the microstructure of FIG. 5.
Figure 7:
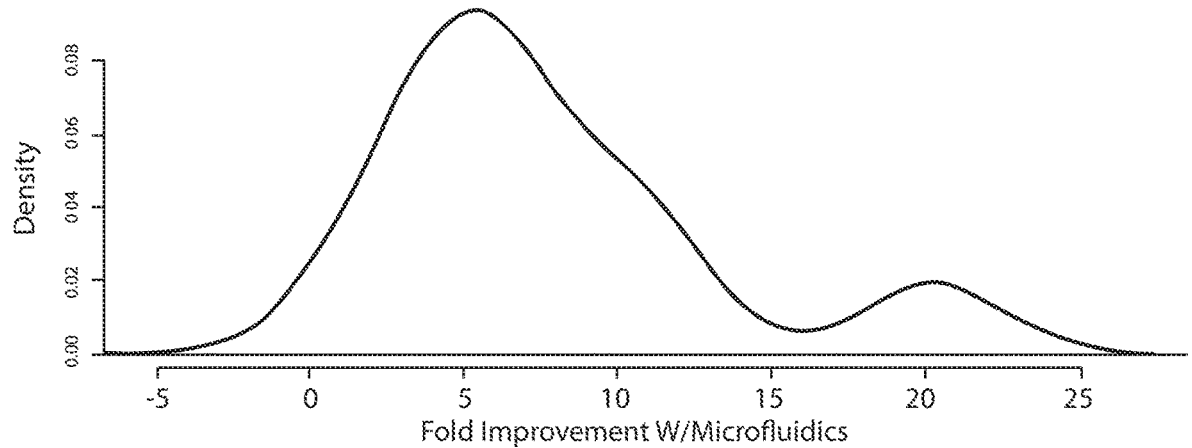
FIG. 7 is a density plot of the fold improvement of sperm sample volumes of a device of the present disclosure compared to conventional counting methods.

FIG. 6 illustrates a side cross sectional view of a portion of the microstructure 520 by the time that the tissue sample reaches or nears the outlets 530a-e. This illustrates the manner in which materials of the tissue sample are arranged and separated for discharge through respective outlets, as further described in PCT App. No. PCT/US15/56494, incorporated herein. That is, one stream is a sperm sample volume discharged through one outlet 530a, and the other streams are discharged out other outlet 530b and 530c. In this configuration, one experiment showed that nearly 82 percent of the sperm cells were collected from outlet 530a, while nearly 90 percent of RBCs were collected from another outlet 530b of the microchannel structure 520.

The system 500 can further comprise a sperm enrichment system or module 510 (e.g., module 310) that is fluidly connected to a sperm sample volume outlet 530a of the plurality of outlets 530a-e. Alternatively, a syringe (or vial) can collect the sperm sample volume from the outlet 530a, and then it can be injected into the enrichment module 510 for enrichment of the sperm sample volume. The sperm enrichment module 510 can comprise a membrane filter 516 (e.g., 316) that filters the sperm sample volume to remove excess media 534 to a collector 538, and to generate or produce an enriched sperm sample volume 511 to a collector 512. Thus, the microfluidic separating system 504 can define a separation stage to separate the tissue sample into a sperm sample volume that can be enriched by a sperm enrichment module 510 that defines an enrichment stage for filtering and enriching the sperm sample volume.

Note that the microfluidic separating system 504 can include any number of suitable inlets and outlets, such as two inlets and four outlets, or two inlets and two outlets, depending on sperm recovery requirements of a particular system. Two syringes can be used to inject tissue samples into two inlets of the microfluidic separating system 504, which can have a calculated flow rate of 0.26 ml/min for each syringe, resulting in a combined flow rate of 0.52 ml/min through the microchannel. And, two or more syringe pumps can be coupled to the outlets 530a-e of the microfluidic separating system 504 for pulling an equal amount of tissue sample volume that is being injected, but at a slower rate (e.g., 0.2 ml/min) to help maintain back pressure. Such back pressure is useful to ensure that fluid pressure is exerted against the radial wall (e.g., 318) of the membrane filter 513 (e.g., 316), for instance, for effective filtering and enriching a sperm sample volume, as exemplified above. Notably, in the above-mentioned examples fluorescence labeling is not utilized such that a fluorescence detector and fluorescence light source are typically not part of the system.

In one experiment that included the microfluidic separating system 504 of FIG. 5 (and the sperm enrichment module 310 of FIG. 3), a total of 10 MicroTESE samples were used for separation and enrichment, each of which was divided into two sub-groups: 1) normal process, and 2) microfluidic processing. Normal processing included collagenase digestion of tissue, placing the sample under oil, and observation on an inverted scope. Microfluidic processing included taking collagenase digested tissue and running this tissue through the system (e.g., 500) followed by observation under oil with an inverted scope. In most cases, sperm from a separate sample was spiked into the sample prior to application to both procedures.

TABLE 1

| Test No. | Disclosed Microfluidics Device | Conventional Device | Fold Improvement |
| --- | --- | --- | --- |
| 1 | 0.363 | 0.033 | 10.90909091 |
| 2 | 0.033 | 0 | (infinity) |
| 3 | 13.6 | 2.3 | 5.913043478 |
| 4 | 0.3667 | 0.0667 | 5.5 |
| 5 | 112 | 5.5 | 20.36363636 |
| 6 | 12.3 | 3.5 | 3.514285714 |
| 7 | 0.8 | 0.5 | 1.6 |
| 8 | 22.9 | 3.4 | 6.735294118 |
| 9 | 10.4 | 1 | 10.4 |
| 10 | 0.5 | 0.1 | 5 |

Table 1 depicts the number of sperm identified per minute in both tests groups; the first being the "test" column that shows results from flowing a sperm tissue sample through a microfluidics device (i.e., separation and enrichment system) of the present disclosure. In every test sample case, sperm was much more quickly identified with the use of the microfluidics device of the present disclosure. The use of the spiral microstructure (e.g., 520) resulted in an average of approximately 7.78 fold improvement in sperm found per unit of time than through conventional techniques. In one of the ten cases, there were sperm identified in a sample from which no sperm were identified via conventional approaches. Both fresh samples and those that had been previously frozen (in test yolk buffer) were used in the study and performed equally well.

Figure 8:
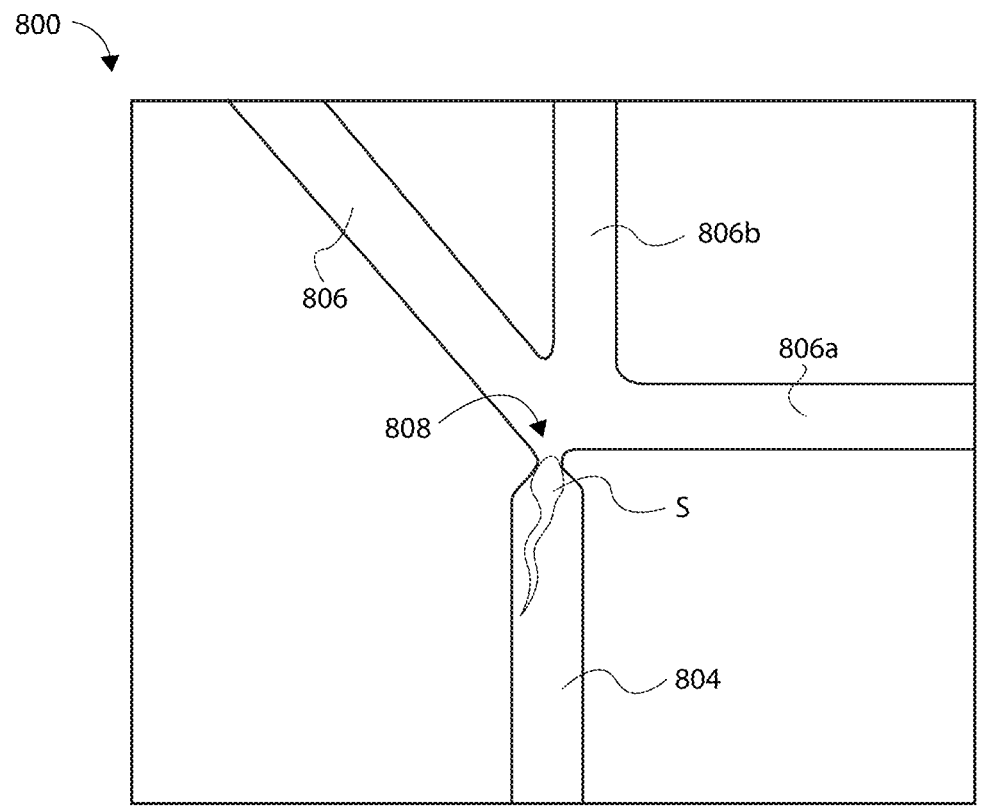
FIG. 8 is a top down view of a section of a microfluidics device or chip for trapping one or more sperm, in accordance with an example of the present disclosure.

FIG. 8 shows a microfluidic device section 800, such as a portion of a microfluidic chip that illustrates the ability to trap a sperm of an enriched sperm sample volume (e.g., 511). Because an in-vitro fertilization (IVF) process is a time-sensitive procedure that benefits from coordination of oocyte collection and sperm preparation, it can be desirable to isolate sperm from microTESE procedures using cryopreservation techniques for later use of the sperm. When sperm are identified within freshly biopsied tissue, current cryopreservation techniques entail bulk tissue storage within relatively large storage tubes. As a consequence, it can be difficult to relocate the sperm once tissue is thawed. In addition, this traditional method allows for only one opportunity to thaw sperm for therapeutic use, because multiple freeze/thaw events can be detrimental to sperm viability. Thus, a closed microfluidic system, including the microfluidic device section 800, of the present disclosure can be capable of processing a very low concentration of sperm (in sperm media) into aliquots (with one sperm in each aliquot) that can be individually cryopreserved and easily recovered post-thaw. For example, such closed microfluidic system, including the microfluidic device section 800, can receive a suspension of 10 sperm as input and produce 2 aliquots of 5 sperm each for individual cryopreservation. In this way, the closed microfluidic system can sort sperm from a low concentration sperm sample (e.g., less than 100 sperm/nil) and then place them in connected cryotips. The closed microfluidic system can include a series of devices based off two designs. The first design is a device in which sperm sorting can performed before the sorted sperm can be transferred to cryotips (e.g., FIG. 8). The second design is a distributor chip (e.g., FIG. 9) that avoids the need to have valves to deliver small numbers of sperm to the cryotips for freezing.

More specifically, the first device consists of a simple microfluidic network with built-in microvalves, such as microvalve 802 shown in FIG. 8, that can trap and then release individual sperm. Specifically, the microfluidic device section 800 can include in input microchannel 804 and output microchannels 806a-c, and a constriction trap channel 808 defining the microvalve 802 formed as a narrow neck or passageway between the input microchannel 804 and the output microchannels 806a-c. The constriction trap channel 808 can have a width of approximately 0.2 μm to 8 μm, in some cases 0.5 to 4 μm, and in one example a width of approximately 1.5 μm. Therefore, as the sperm S travels through the input microchannel 804, is it restricted from passing through the constriction trap channel 808, because the sperm S dimensions can be ~3 μm, which is larger than an example 2 μm width of the constriction trap channel 808. This "traps" one or more sperm proximate constriction trap channel 808. Once a sperm (or a group of sperm) are trapped at one or more the constriction trap channels (e.g., like 808), the fluid flow in the channels and the trap can be reversed and sperm are released from the trap. The released sperm can then be routed in a microfluidic network to a cryotip (connected to the microfluidic chip or closed microfluidic system) by controlling a series of microvalves, such as through implementation of a LabView software/hardware setup. The final result is a microfluidic chip or system that can trap individual sperm from low concentration sperm samples and place trapped sperm in cryotips for subsequent cryopreservation. Since the application of the microfluidic chip is to trap and sort sperm from microTESE samples (with <100 sperm/ml) the microfluidic chip can operate with concentrations of ~20 sperm/ml and ~100 sperm/ml.

It is typically important that sperm maintain viability as they are trapped and sorted by such microfluidic chip described above. In one experiment, five sets of readings were taken that included percentage of sperm with progressive motility at two locations on a microfluidic chip before and after a group of sperm (~60 in number) were trapped. Experiments were performed in which an observed number of sperm were trapped, collected and then transported into the attached cryotip, with about 0.5 μl of solution collected in the cryotip. Afterwards the cryotip is separated from the microfluidic chip, the collected solution in the cryotip was dispensed on a microscope slide and the number of sperm in the dispensed volume were counted to verify both collection and the ability to recover the sperm.

In testing of different sizes of constriction trap channels (e.g., 808), sizes between 0.6 μm and 1.5 μm are particularly effective, which is likely due to the inherent expansion of PDMS in a pressure flow and the deformability of sperm. Furthermore, based on experiments, a channel height of less than 5 μm may inhibit smooth flow of sperm in the chip and can lead to channel clogs, so the height of a channel (e.g., input channel 804 and/or microchannels 806a-c) can often be 5 μm or more. In some examples, a particular microfluidic device or chip can trap single sperm (see FIG. 8)) or multiple sperm in a single sperm trap at sample concentrations of ~20 sperm/ml, and ~100 sperm/ml. Regarding motility, the sperm in the above experiments were found to maintain motility before and after being trapped and sorted by the microfluidic device.

As noted above, microfluidic device clogging can be frequently encountered in the tests of a sperm sorting system or chip. Thus, a separated and enriched volume of sperm can be transferred from the system described above (e.g., FIG. 5) to a set of cryotips for subsequent cryopreservation using the distribution device 900 of FIG. 9. The distribution device 900 can distribute a 50-100 μl volume of a separated/enriched sperm volume into cryotips without any sperm trap (e.g., without using the trap shown in FIG. 8). The distribution of a separated/enriched sperm volume can be carried out by utilizing a laminar flow profile. The distribution device 900 can be made partly in PDMS and partly in glass. The distribution device 900 can include an input channel 902, two intermediary channels 904a and 904b, and four branch channels 906a-d that extend from the two intermediary channels 904a and 904b. Each of the four branch channels 906a-d in the network can have a certain depth (e.g., 5 μm to 10 μm and in some cases 11 μm to 25 μm), which allows for the provision for sperm to sink to the bottom of the branch channels where they can be identified through an inverted microscope. This allows clinicians to potentially identify the number sperm in each branch before the sample is loaded in the respective cryotip for cryopreservation. In addition, this design avoids clogging of the branch channels 906a-d with cellular debris that is commonly present in clinical samples, which could lead to loss of sperm. Experimental results show distributing a 50 μl sample (with ~1000-5000 sperm/nil) to four aliquots via the four branch channels 906a-d.

Figure 9:
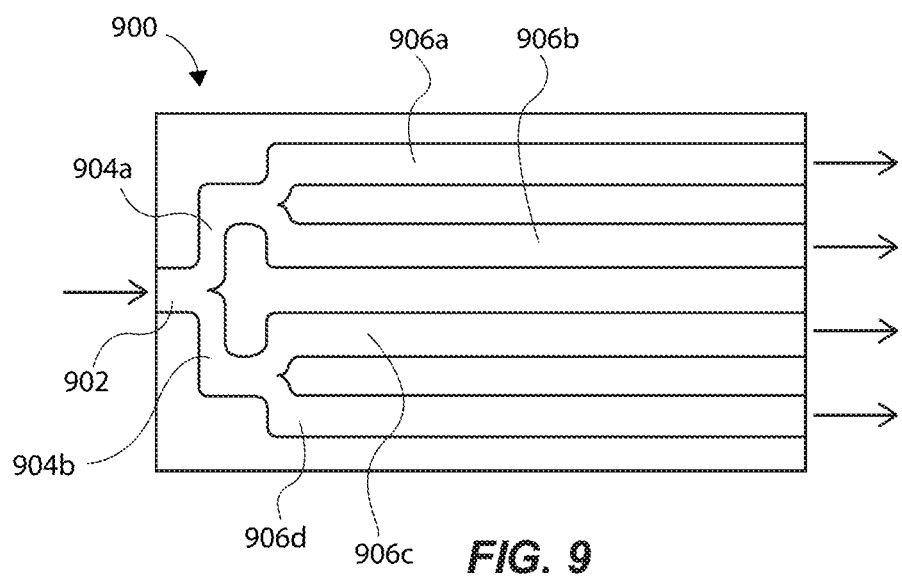
FIG. 9 is a top down view of a distribution device or chip for distributing an enriched sperm sample volume, in accordance with an example of the present disclosure.

Therefore, whether using the "trap" microfluidic device of FIG. 8, or the distribution device 900 of FIG. 9, a relatively small amount of an enriched sperm sample volume (e.g., 50

μl) can be cryopreserved after efficient separation and enrichment of a sperm sample volume is provided to a cryotip, as detailed above, without substantial loss of sperm and/or motility, and without a noticeable amount of media debris in the sperm sample volume.

The separation and enrichment systems and methods exemplified herein are beneficial over traditional counting processes that omit non-motile viable sperm for microTESE samples from azoospermic men with large numbers of non-motile sperm originating from testicular tissue, because the present separation and enrichment systems are capable of processing testicular biopsy samples to isolate sperm from other cells or cellular debris irrespective of sperm motility. This is because the devices exemplified herein dramatically reduce the volume of typical biopsy samples (e.g., reductions to volumes from 10 μl to 2 ml) which leads to significantly reduced time (e.g., reduce to 20-30 minutes) required by a technician searching/counting sperm in traditional methods for preservation.

In one example, approximately 1 ml of diluted tissue sample can be processed through a microfluidic separating and enrichment system to produce an enriched sperm sample volume of approximately 20 μl to 100 μl, and preferably approximately 50 μl (of which mature sperm are targeted for enrichment). This is not achievable with existing processing systems for microTESE sperm samples due to their lack of enrichment processing (e.g., membrane filter), and due to omission of non-motile viable sperm for microTESE samples from azoospermic men with large numbers of non-motile sperm originating from testicular tissue. Furthermore, the devices exemplified herein can significantly enrich the final sample (e.g., the enriched sperm sample volume) with sperm while removing other debris (i.e., via a membrane filter), therefore "cleaning" the sperm sample volume and increasing the likelihood of identifying sperm in the lower volume sample.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A method of separating and enriching sperm from a tissue sample, comprising:
   obtaining a microfluidic separating system having an inlet end and an outlet end, wherein a membrane filter is fluidly connected to the outlet end;
   separating the tissue sample via the microfluidic separating system into a debris fluid volume comprising little to no sperm and a sperm fluid volume comprising sperm at a higher concentration than in the debris fluid volume; and
   enriching the sperm fluid volume by removing excess media via the membrane filter.

2. The method of claim 1, wherein obtaining the microfluidic separating system comprises coupling a sperm enrichment module, supporting the membrane filter, to the outlet end of a microchannel structure of the microfluidic separating system.

3. The method of claim 1, wherein enriching the sperm fluid volume further comprises flowing the sperm fluid volume through a tube having a radial wall comprising the membrane filter, such that excess media is filtered through the radial wall and to a discharge outlet, and such that an enriched sperm fluid volume is discharged through an axial collection outlet to produce the enriched sperm fluid volume.

4. The method of claim 1, wherein separating the tissue sample comprises flowing the tissue sample through a separation fluid channel of a microchannel structure of the microfluidic separating system.

5. The method of claim 4, wherein flowing the tissue sample through the separation fluid channel comprises flowing the tissue sample through a spiral separation fluid channel and under laminar flow conditions, wherein a cross-flow in the spiral separation fluid channel facilitates segregation of tissue sample into the sperm fluid volume that is then flowed through the membrane filter.

6. The method of claim 1, wherein the membrane filter comprises a hollow fiber membrane filter comprising pores operable to permit passage of excess debris based on size, and to restrict passage of sperm.

7. The method of claim 1, wherein, after enriching the sperm fluid volume, the method further comprises trapping at least one sperm of the sperm fluid volume with a microfluidic valve of a microfluidic chip, and then backflowing a microfluidic channel of the microfluidic chip to release the trapped at least one sperm to collect the at least one sperm.

8. The method of claim 1, wherein enriching the sperm fluid volume generates an enriched sperm fluid volume, the method further comprising flowing the enriched sperm fluid volume through an inlet of a distribution device comprising a plurality of separate microchannels for separation and collection of the enriched sperm fluid volume.

9. The method of claim 1, further comprising flowing approximately 1 ml of diluted tissue sample through the microfluidic separating system to produce an enriched sperm sample volume of approximately 20 μl to 100 μl.

10. The method of claim 1, wherein the method is free of fluorescence detection of labeled material within the tissue sample.

11. A two-stage tissue sample separation system, comprising:
   a microchannel structure defining a separation fluid channel to form a separation stage;
   an inlet end of the microchannel structure;
   an outlet end of the microchannel structure; and
   a membrane filter fluidly connected to the outlet end, the membrane filter defining an enrichment stage downstream of the separation stage;
   wherein flow of the tissue sample through the separation stage facilitates at least partial segregation of materials in the tissue sample based on size, and wherein subsequent flow of the tissue sample through the enrichment stage further facilitates removal of at least a portion of excess media in the tissue sample via the membrane filter, the excess media comprising little to no sperm such that the tissue sample has a higher concentration of sperm than in the excess media.

12. The system of claim 11, wherein the membrane filter comprises a tube having a radial wall at least partially formed of a hollow fiber membrane filter material having pores sized to permit passage and restrict passage of materials in the tissue sample based on size.

13. The system of claim 11, further comprising a sperm enrichment module comprising the membrane filter, wherein the sperm enrichment module defines the enrichment stage, and comprises at least one media discharge connector coupled to the membrane filter, the at least one media discharge connector comprising a discharge outlet for discharging excess media to a waste collector.

14. The system of claim 13, wherein the sperm enrichment module comprises a plurality of media discharge connectors arranged in series and coupled together by tube sections, wherein the medial discharge connectors are fluidly connected to the tube sections, and wherein each media discharge connector comprises a T-port connector having a discharge outlet.

15. The system of claim 13, wherein the sperm enrichment module defines an excess media flow path and an enriched sperm fluid flow path, wherein the excess media flow path extends from the outlet end of the microchannel structure through pores of the membrane filter and out through the discharge outlet, and wherein the enriched sperm fluid flow path extends centrally through a primary flow channel of the membrane filter to an enrichment outlet of the sperm enrichment module.

16. The system of claim 13, wherein the microchannel structure comprises a plurality of outlets, wherein a sperm sample outlet of the plurality of outlets is in fluid communication with an inlet of the membrane filter of the sperm enrichment module.

17. The system of claim 11, wherein the membrane filter comprises an elongate tube.

18. The system of claim 13, wherein the at least one media discharge connector comprises a support body having an open area adjacent an outer surface of the membrane filter, such that excess debris filtered through the membrane filter flows through the open area and out a discharge outlet of the support body.

19. The system of claim 11, wherein the microchannel structure comprises a spiral configuration.

20. The system of claim 11, further comprising a microfluidic separating system comprising the microchannel structure, the microfluidic separating system comprising:
 an inlet zone proximate the inlet end, and having a carrier fluid inlet to receive the carrier fluid and a tissue sample inlet to receive the tissue sample;
 an outlet zone having a plurality of outlets proximate the outlet end; and
 a transport region between the inlet zone and the outlet zone, the transport region being open to the carrier fluid and the tissue sample, wherein a cross-flow in the transport region facilitates segregation of the materials in the tissue sample based on size,
 wherein the membrane filter is in fluid communication with a sperm sample outlet of the plurality of outlets, such that the sperm sample volume of the tissue sample is transferable through the sperm sample outlet to the membrane filter for enriching the sperm sample volume.

21. The system of claim 13, further comprising a microfluidic chip comprising an inlet channel in fluid communication with an outlet of the membrane filter of the enrichment module, the microfluidic chip comprising a microfluidic valve operable to trap at least one sperm of the enriched sperm sample volume.

22. The system of claim 11, wherein the system does not include a fluorescence detector or a fluorescence light source.

23. The system of claim 1, wherein the tissue sample comprises a microTESE sample.

24. The system of claim 23, wherein the microTESE sample comprises sperm cells, red blood cells, tissue debris, and a carrier fluid.

* * * * *